United States Patent
Wüstling et al.

(10) Patent No.: US 6,555,130 B2
(45) Date of Patent: Apr. 29, 2003

(54) PROCESS FOR THE CONTINUOUS PRODUCTION AND COATING OF SELF-ADHESIVE COMPOSITIONS BASED ON POLYISOBUTYLENE WITH AT LEAST ONE ACTIVE PHARMACEUTICAL SUBSTANCE

(75) Inventors: Jens-Uwe Wüstling, Hamburg (DE); Matthias Wasner, Hamburg (DE); Joachim Kirchner, Uetersen (DE); Reinhard Uphus, Hannover (DE); Sören Struckmann, Steinhude (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/759,559

(22) Filed: Jan. 12, 2001

(65) Prior Publication Data
US 2001/0039302 A1 Nov. 8, 2001

(30) Foreign Application Priority Data
Jan. 14, 2000 (DE) .......................... 100 01 546

(51) Int. Cl.[7] .................. A61F 13/02; A61L 3/00; C08F 26/04
(52) U.S. Cl. ............... 424/448; 424/449; 424/443; 427/2.31; 525/285; 525/242
(58) Field of Search ............... 424/948, 449, 424/443

(56) References Cited

U.S. PATENT DOCUMENTS

| | | | |
|---|---|---|---|
| 4,192,785 A | 3/1980 | Chen et al. | 260/17.4 |
| 4,253,460 A | 3/1981 | Chen et al. | 128/283 |
| 5,126,144 A | 6/1992 | Jaeger et al. | 424/448 |
| 5,424,367 A * | 6/1995 | Auda et al. | 525/242 |
| 5,539,033 A | 7/1996 | Bredahl et al. | 525/270 |
| 5,550,175 A | 8/1996 | Bredahl et al. | 523/348 |
| 5,679,373 A * | 10/1997 | Wick et al. | 424/448 |
| 5,866,249 A * | 2/1999 | Yarusso et al. | 428/343 |

FOREIGN PATENT DOCUMENTS

| | | | |
|---|---|---|---|
| DE | 28 25 195 | 12/1978 | A61L/15/06 |
| DE | 37 43 946 | 3/1989 | A61L/15/06 |
| DE | 198 06 609 | 8/1999 | C09J/201/00 |
| WO | 9411175 | 5/1994 | B29C/47/10 |
| WO | 9525774 | 9/1995 | C09J/5/08 |
| WO | 9707963 | 3/1997 | B29C/47/10 |

* cited by examiner

Primary Examiner—Thurman K. Page
Assistant Examiner—Isis Ghali
(74) Attorney, Agent, or Firm—Norris McLaughlin & Marcus

(57) ABSTRACT

A process for the continuous solvent-free and mastication-free production of self-adhesive compositions based on polyisobutylene with at least one active pharmaceutical substance in a continuously operating apparatus having a filling section and a compounding section, comprising the following steps:

a) feeding an initial batch comprising granulated polyisobutylene, at least one release auxiliary and at least one active pharmaceutical substance into the filling section of the apparatus;

if desired, feeding low molecular mass polyisobutylene, fillers, plasticizers, tackifiers and/or resins, b) transferring the feed components of the self-adhesive composition from the filling section to the compounding section, c) if desired, adding the components of the self-adhesive composition that have not been introduced in the filling section, such as low molecular mass polyisobutylene, fillers, plasticizers, tackifiers and/or resins, to the compounding section, d) if desired, adding further pharmaceutical substances to the compounding section of the apparatus, e) preparing a homogeneous self-adhesive composition in the compounding section, and f) discharging the self-adhesive composition.

20 Claims, 1 Drawing Sheet

PROCESS FOR THE CONTINUOUS PRODUCTION AND COATING OF SELF-ADHESIVE COMPOSITIONS BASED ON POLYISOBUTYLENE WITH AT LEAST ONE ACTIVE PHARMACEUTICAL SUBSTANCE

The present invention relates to a process for the continuous production and coating of self-adhesive compositions based on polyisobutylene with at least one active pharmaceutical substance.

Fundamental to the profile of performance requirements of pressure sensitive adhesive systems and the pressure sensitive adhesive articles produced with them (such as patches, for example) are the two physical phenomena of adhesion and cohesion of the pressure sensitive adhesive layers. Adhesion is dealt with in the technical jargon using the terms instant bond strength (tack) and bond strength (peel strength) and describes by definition the terms "self-adhesive", "pressure sensitive adhesive" and/or "pressure sensitive adhesive tapes", i.e., permanent adhesive bonding under "gentle pressure".

Especially in the case of pressure sensitive adhesives based on rubber, this property is obtained by mixing in tackifying resins (tackifiers) and plasticizers having relatively low molecular weights.

The second defining property of the pressure sensitive adhesives is their simple residue-free redetachability after use. This property is determined essentially by the high molecular mass rubber fractions as the elastomer component, which give the system, in the form of cohesion (internal strength), the required strength under shear stress, which is of particular significance for the use of the products under mechanical loads.

The performance of the pressure sensitive adhesive is, therefore, critically determined by the balanced proportion of adhesion properties and cohesion properties and by compatibility, homogeneity and stability of the blend of components with extremely high and relatively low average molecular weights, something which is relatively easy to achieve when the composition is produced in industry-standard mixers and kneading machines using solvents.

The advantage of foregoing the use of solvents lies essentially in the simplification of the coating process. The avoidance of flammable solvents does away with the need for the drier units, with their high energy consumption for the evaporation and recovery of the solvents, and with the need to use explosion-protected units. Hot-melt coating units are compact and permit much higher coating speeds. The technology is an environment-friendly one in which there are no solvent emissions. Furthermore, no unwanted solvent residues remain in the self-adhesive composition. This is the reason for the reduction in the allergenic potential of the product.

For the solvent-free compounding, the prior art makes use predominantly of block copolymers having polystyrene block fractions, or natural and/or synthetic rubbers.

Owing to the high molecular mass fractions of the rubber (with $M_w \geq 3*10^5$ g/mol), solvent-free self-adhesive compositions cannot be processed by the hot-melt pressure sensitive adhesive technology, or else the rubbers used must be reduced in their molecular weight (broken down) severely before processing.

The deliberate industrial process of rubber breakdown under the combined action of shear stress, temperature and atmospheric oxygen is referred to in the technical literature as mastication and is generally carried out in the presence of chemical auxiliaries, which are known from the technical literature as masticating agents or peptizers, or, more rarely, as "chemical plasticizing agents". In rubber technology, the mastication step is necessary in order to make it easier to integrate the additives.

According to Römpp (Römpp Lexikon Chemie—Version 2.0, Stuttgart/New York: Georg Thieme Verlag 1999), mastication is a term used in rubber technology for the breaking down of long-chain rubber molecules in order to increase the plasticity and/or reduce the (Mooney) viscosity of rubbers. Mastication is carried out by treating, in particular, natural rubber in kneading apparatus or between rolls at very low temperatures in the presence of mastication aids (masticating auxiliaries). The high mechanical forces which act lead to a "tearing apart" of the rubber molecules, with the formation of macroradicals, whose recombination is prevented by reaction with atmospheric oxygen. Mastication aids such as aromatic or heterocyclic mercaptans and their zinc salts or disulfides accelerate the mastication process by promoting the formation of primary radicals. Activators such as metal (iron, copper, cobalt) salts of tetraazaporphyrins or phthalocyanines enable the mastication temperature to be lower. For the mastication of natural rubber, mastication aids are used in amounts of from about 0.1 to 0.5% by weight in the form of masterbatches, which facilitate a uniform distribution of this small amount of chemicals within the rubber composition.

Mastication must be clearly distinguished from the breakdown known as degradation which results in all of the standard solvent-free polymer technologies, such as compounding, conveying and coating in the melt.

Degradation is a collective term for various processes which change the appearance and properties of plastics. Degradation may be caused, for example, by chemical, thermal, oxidative, mechanical or biological influences or else by the effect of rays (such as (UV) light). Examples of consequences are oxidation, chain cleavages, depolymerization, crosslinking, and/or elimination of side groups of the polymers. The stability of polymers with respect to degradation may be increased by using additives, for example, by adding stabilizers such as antioxidants or light stabilizers.

A variety of routes to the solvent-free production and processing of rubber pressure sensitive adhesives have been described.

The patent CA 698 518 describes a process for achieving a composition by adding high proportions of plasticizer and/or simultaneously strong mastication of the rubber. Although this process may be used to obtain pressure sensitive adhesives having an extremely high tack, a user-compatible shear strength can be achieved only to a limited extent, even with a relatively high level of subsequent crosslinking, owing to the relatively high plasticizer content or else to the severe breakdown in molecular structure of the elastomer to a molecular weight average of $M_w \leq 1$ million.

The use of polymer blends, where besides nonthermoplastic natural rubber use is also made of block copolymers, in a ratio of approximately 1:1, is essentially an unsatisfactory compromise solution, since it results neither in high shear strengths when the self-adhesive tapes are used at relatively high temperatures nor in significant improvements relative to the properties described in the patent.

The use of exclusively non-thermoplastic rubbers as the elastomer component in the formulation of pressure sensitive adhesives with the existing cost advantage possessed by, for example, natural rubbers over the standard commercial block copolymers, and the outstanding properties, especially the shear strength of natural rubber and of corresponding synthetic rubbers, is also set out at length in the patents WO 94 11 175 A1, WO 95 25 774 A1, WO 97 07 963 A1 and, correspondingly, U.S. Pat. No. 5,539,033 and U.S. Pat. No. 5,550,175.

In these cases, the additives customary in pressure sensitive adhesive technology, such as tackifier resins, plasticizers and fillers, are described.

The production process disclosed in each case is based on a twin-screw extruder which permits compounding to a homogeneous pressure sensitive adhesive blend with the chosen process regime, involving mastication of the rubber and subsequent gradual addition of the individual additives with an appropriate temperature regime.

The mastication step of the rubber, which precedes the actual production process, is described at length. It is necessary and characteristic of the process chosen, since with the technology chosen therein it is indispensable to the subsequent integration of the other components and to the extrudability of the blended composition. Also described is the feeding in of atmospheric oxygen, as recommended by R. Brzoskowski, J. L. and B. Kalvani in Kunststoffe 80 (8), (1990), p. 922 ff., in order to accelerate mastication of the rubber.

This procedure makes it absolutely necessary to practice the subsequent step of curing by electron beam crosslinking (EBC) and to use reactive substances as EBC promoters in order to achieve an effective crosslinking yield.

Both process steps are described in the abovementioned patents, but the EBC promoters chosen also tend toward unwanted chemical crosslinking reactions at elevated temperatures, which limits the use of certain tackifying resins.

The object of the present invention is to provide a process with which pressure-sensitive self-adhesive compositions based on polyisobutylene and comprising at least one active pharmaceutical ingredient can be produced continuously without solvent and, if desired, can be coated in-line without the need for property-impairing mastication of the polyisobutylene.

This object is achieved by a process as set out in the main claim. Claim 2 describes the process with minor adaptations. The dependent claims relate to advantageous developments of the processes.

The invention accordingly provides a process for the continuous solvent-free and mastication-free production of self-adhesive compositions based on polyisobutylene with at least one active pharmaceutical substance in a continuously operating apparatus having a filling section and a compounding section, comprising the following steps:

a) feeding an initial batch comprising granulated polyisobutylene, at least one release auxiliary and at least one active pharmaceutical substance into the filling section of the apparatus;

if desired, feeding low molecular mass polyisobutylene, fillers, plasticizers, tackifiers and/or resins, b) transferring the feed components of the self-adhesive composition from the filling section to the compounding section, c) if desired, adding the components of the self-adhesive composition that have not been introduced in the filling section, such as low molecular mass polyisobutylene, fillers, plasticizers, tackifiers and/or resins, to the compounding section, d) if desired, adding further pharmaceutical substances to the compounding section of the apparatus, e) preparing a homogeneous self-adhesive composition in the compounding section, and f) discharging the self-adhesive composition.

The invention additionally embraces a process for the continuous solvent-free and mastication-free production of self-adhesive compositions based on polyisobutylene with at least one active pharmaceutical substance in a continuously operating apparatus having a filling section and a compounding section, comprising the following steps:

a) feeding an initial batch comprising granulated polyisobutylene, at least one release auxiliary into the filling section of the apparatus; if desired, feeding low molecular mass polyisobutylene, fillers, plasticizers, tackifiers and/or resins, b) transferring the feed components of the self-adhesive composition from the filling section to the compounding section, c) adding at least one pharmaceutical substance to the compound section and, if desired, adding the components of the self-adhesive composition that have not been introduced in the filling section, such as low molecular mass polyisobutylene, fillers, plasticizers, tackifiers and/or resins, to the compounding section, d) preparing a homogeneous self-adhesive composition in the compounding section, and e) discharging the self-adhesive composition.

The addition of at least one active pharmaceutical substance to the compounding section, and the possibly necessary addition to the compound section of components of the self-adhesive composition which have not been introduced in the filling section, such as low molecular mass polyisobutylene, fillers, plasticizers, tackifiers and/or resins, may take place over the entire length of the compounding section. In particular, a plurality of metering points are possible, so that each individual component may be metered in specifically via a separate feed depending on the requirements of the process regime.

It has been found particularly advantageous to use a twin screw extruder having at least one metering port, preferably between two and seven, and at least one devolatilization aperture, as the continuously operating apparatus.

Moreover, the temperature in the apparatus should not exceed 150° C., preferably not 140° C., with particular preference not 130° C., in order to rule out thermal damage to, in particular, the active substance or substances.

In one advantageous embodiment of the process, a melt pump or extruder is arranged between the apparatus and the coating device in order to convey the self-adhesive compositions.

In the second process step, which takes place advantageously in connection with the compounding step in the twin screw extruder, the self-adhesive composition prepared in accordance with the invention is coated in a solvent-free manner onto a backing in web form, onto a release film or onto a release paper, using an applicator unit. Coating may take place over the full area or else partially.

In order to obtain a defined, air-bubble-free application of composition to the web-form material, it is advantageous for the self-adhesive composition to be subjected to devolatilization before entering the coating unit, something which is particularly important when inert gases are used during the compounding process in the twin screw extruder. In accordance with the process of the present invention, devolatilization may take place under the influence of subatmospheric pressure or to the atmosphere, preferably in screw machines.

At the exit from the apparatus, the self-adhesive composition preferably has a temperature of less than 150° C., more preferably less than 130° C., with particular preference less than 110° C.

Various processes are suitable for coating onto web-form materials. Solvent-free self-adhesive compositions may be coated by means of an extrusion die downstream of the twin screw extruder. For the pressure buildup for the die coating, single screw extruders and/or melt pumps are particularly preferred, so that the web-form backing materials may be coated with composition application rates with a very low breadth of fluctuation.

A further possibility for coating web-form backing materials with the active substance self-adhesive composition prepared in accordance with processes of the invention is the use of roll coating applicator units or multiroll coating calenders, consisting preferably of at least two coating rolls, the self-adhesive composition being formed to the desired thickness as it passes through one or more roll nips prior to transfer to the web-form material. This coating process is particularly preferred when coating with extrusion dies alone no longer provides the required accuracy in the amount of composition applied. Depending on the nature of the web-form backing material to be coated, coating may take place in a co-rotational or counter-rotational process.

Coating is possible on roller coating applicator units or multiroll coating calenders at temperatures below 150° C., so that it is also possible to coat self-adhesive compositions which comprise thermally sensitive active substances. For the purpose of increased gas bubble freedom of the coated adhesive composition, it is possible to install a vacuum devolatilizer, for example, a vacuum chamber, a devolatilizing extruder, air knives or the like, between twin screw extruder and applicator unit.

In accordance with the process of the present invention, there is no property-impounding mastication of the polyisobutylene, since the addition of the liquid components is made shortly after the polyisobutylene feed. These liquid components may comprise both low molecular mass polyisobutylene, plasticizers and/or tackifiers, and resins which melt only during the compounding process under the action of shear energy and/or external heating. Owing to the presence of these liquid components, the extent of frictional energy is limited in such a way that it is possible to prevent the mastication of polyisobutylene and also high resulting compounding temperatures. In the individual process steps, however, degradation processes may occur, but do not permanently impair the properties of the self-adhesive composition.

The twin screw extruder should have one or, preferably, a plurality of separate temperature control or cooling circuits in order to permit a temperature regime which allows the use of thermally sensitive active pharmaceutical substances. In cases where this is unnecessary, the temperature control circuits may also be combined with one another in order to minimize the number of temperature control devices.

The process of the invention permits the preparation of self-adhesive compositions with active pharmaceutical substances and, especially in conjunction with a downstream coating unit, the production of self-adhesive articles which in turn are used to produce patches or bandages, while achieving particular cost advantages.

The process consists essentially of the steps set out already, which optionally may be conducted under an inert gas atmosphere in order to prevent oxidative polymer degradation.

In the compounding step, a composition comprising polyisobutylenes, one or more active pharmaceutical substances, and the required adjuvants such as low molecular mass polyisobutylene, fillers, plasticizers, tackifiers and/or resins, is produced without solvent preferably in a twin screw extruder, the composition having a final temperature of less than 150° C., preferably less than 130° C., with very particular preference less than 110° C. The active pharmaceutical substances here may be added directly at the beginning of the process, but may also—depending on the sensitivity of the active substance—be introduced into the twin screw extruder only at a later point in time. The addition may be made in straight or dissolved form.

In accordance with the invention, the self-adhesive composition is based on polyisobutylene.

According to Römpp Lexikon Chemie (Version 2.0, Stuttgart/New York: Georg Thieme Verlag 1999) the term polyisobutenes or polyisobutylenes (PIB) is used to refer to the polymers, counted among the polyolefins, of the structure

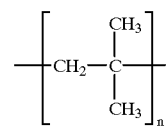

which are prepared by cationic polymerization of isobutene. Standard commercial PIBs may be classified in 3 product categories:

oily liquids (molar mass: 300–3000 g/mol)

viscose tacky masses (molar mass: 40,000–120,000 g/mol)

rubberlike elastic masses (molar mass: 300,000–2,500,000 g/mol)

The different molar masses may be adjusted during the polymerization by using regulators (for example, 2,4,4-trimethyl-1-pentene, "diisobutene").

To modify the PIB properties, isobutene may be copolymerized with appropriate copolymers [for example, styrene and styrene derivatives, isoprene, indene, 1,3-butadiene, cyclopentadiene, etc.]. The copolymers which are of technical interest generally contain >90% isobutene.

The fraction of the high molecular mass granulated polyisobutylene is in particular between 5% by weight and 30% by weight, preferably between 10% by weight and 20% by weight.

The fraction of the low molecular mass polyisobutylene is in particular between 20% by weight and 60% by weight, preferably between 30% by weight and 50% by weight.

Suitable fillers are free-flowing bulk materials and also mixtures thereof, such as cellulose, silica, alginates and pectins, which are not soluble in the adhesive matrix. The filler fraction is in particular between 0% by weight and 60% by weight, preferably between 0% by weight and 40% by weight, with particular preference between 10% by weight and 40% by weight.

Tackifying resins which can be used are, without exception, all tackifier resins known to date and described in the literature. Representatives that may be mentioned include the rosins, their disproportionated, hydrogenated, polymerized and esterified derivatives and salts, the aliphatic and aromatic hydrocarbon resins, terpene resins and terpene-phenolic resins. Any desired combinations of these and other resins can be used in order to adjust the properties of the resultant adhesive composition in accordance with what is desired. Reference may be made expressly to the depiction of the state of knowledge in "Handbook of Pressure Sensitive Adhesive Technology" by Donatas Satas (van Nostrand, 1989).

The resin fraction is in particular between 0% by weight and 50% by weight, preferably between 0% by weight and 40% by weight, with particular preference between 10% by weight and 40% by weight.

Suitable tackifiers are all known tackifying polymers, from the group, for example, of the polyisoprenes, polybutadienes and polyacrylates. The tackifier fraction is in particular between 0% by weight and 50% by weight, preferably between 0% by weight and 40% by weight, with particular preference between 5% by weight and 30% by weight.

Plasticizers which can be used are all known plasticizing substances and also pharmaceutical auxiliaries. They include, inter alia, the paraffinic and naphthenic oils, (functionalized) oligomers such as oligobutadienes and oligoisoprenes, liquid nitrile rubbers, liquid terpene resins, animal and vegetable oils and fats, fatty acid esters, phthalates, alcohols, and functionalized acrylates. The plasticizer fraction is in particular between 0% by weight and 30% by weight, preferably between 2% by weight and 20% by weight.

Active pharmaceutical substances are substances which in human or animal organisms are used to prevent, heal alleviate or detect diseases. The active pharmaceutical substances used may include those having both a systemic and a local activity.

Typical active substances used in accordance with the invention are the following:
aceclidine, amfetaminil, amfetamine, amyl nitrite, apophedrine, atabrine, alprostadil, azulene, arecoline, anethole, amylene hydrate, acetylcholine, acridine, adenosine triphosphoric acid, L-malic acid, alimemazine, allithiamine, allyl isothiocyanate, aminoethanol, apyzine, apiole, azatadine, alprenolol, ethinazone, benzoyl peroxide, benzyl alcohol, bisabolol, bisnorephedrine, butacetoluide, benactyzine, camphor, colecalciferol, chloral hydrate, clemastine, chlorobutanol, capsaicin, cyclopentamine, clobutinol, chamazulene, dimethocaine, codeine, chlorpromazine, quinine, chlorothymol, cyclophosphamide, cinchocaine, chlorambucil, chlorphenesin, diethylethane, divinylethane, dexchlopheniramine, dinoprostone, dixyrazine, ephedrine, ethosuximide, enallylpropymal, emylcamate, erythrol tetranitrate, emetine, enflurane, eucalyptol, etofenamate, ethylmorphine, fentanyl, fluanisone, guaiazulene, halothane, hyoscyamine, histamine, fencarbamide, hydroxycaine, hexylresorcinol, isoaminile citrate, isosorbide dinitrate, ibuprofen, iodine, iodoform, isoaminile, lidocaine, lopirine, levamisole, methadone, methyprylon, methylphenidate, mephenesin, methylephedrine, meclastine, methopromazine, mesuximide, nikethamide, norpseudoephedrine, menthol, methoxyfluran, methylpentinol, metixene, mesoprostol, oxytetracaine, oxyprenolol, oxyphenbutazone, oxyquinoline, pinene, prolintane, procyclidine, piperazine, pivazide, phensuximide, procaine, phenindamine, promethazine, pentetrazole, profenamine, perazine, phenol, pethidine, pilocarpine, prenylamine, phenoxybenzamine, Resochin, scopolamine, salicylic acid ester, sparteine, trichloroethylene, timolol, trifluperazine, tetracaine, trimipramine, tranylcypromine, trimethadione, tybamate, thymol, thioridazine, valproic acid and verapamil, and also other active substances familiar to the skilled worker that can be absorbed through the skin, including the mucous membranes. This list is of course not exhaustive.

The active substance fraction in the self-adhesive composition is preferably between 0.001% by weight and 60% by weight, more preferably between 0.001% by weight and 20% by weight, with particular preference between 0.001% by weight and 10% by weight.

Depending on the intended use, suitable web-form backing materials for the self-adhesive compositions processed and produced in accordance with the invention are all known backings, with or without appropriate chemical or physical surface pretreatment of the coating side, and also antiadhesive physical treatment or coating of the reverse side. Mention may be made, for example, of creped and non-creped papers, polyethylene, polypropylene and mono- or biaxially oriented polypropylene films, polyester, PVC and other films, foam materials in web form, made from polyethylene and polyurethane, for example, wovens, knits and nonwovens.

Finally, the web-form material may be a material with an antiadhesive coating on both sides, such as a release paper or a release film. If desired, the coated backing material is lined with a further release film or a further release paper.

The thickness of the self-adhesive composition on the web-form material may be between 10 $\mu$m and 2000 $\mu$m, preferably between 100 $\mu m$ and 500 $\mu$m.

The intention of the examples which follow is to describe the invention in more detail, without wishing thereby to restrict the invention.

EXAMPLE 1

A prototype was produced using a twin screw extruder from the company Berstorff with a screw diameter of 25 mm, employing the following exemplary formulation A:

| No. | Component | | Weight fraction in % |
|---|---|---|---|
| 1 | Vistanex ® MM L-80 | high molecular mass polyisobutylene | 12 |
| 2 | Vistanex ® LM MH | low molecular mass polyisobutylene | 38 |
| 3 | Hi-Sil ® 233 D | Filler | 14.5 |
| 4 | AVICEL ® PH101 | Filler | 14.5 |
| 5 | Escorez ® E-1310 | Resin | 14 |
| 6 | Whitemor WOM 14 | Plasticizer | 2 |
| 7 | Ibuprofen | active pharmaceutical substance | 5 |

Component 1 was granulated and provided with 5% by weight of component 4 as release agent. Using components 1, 3, 4, 5, 6 and 7, a homogeneous initial batch was produced.

Figure 1:
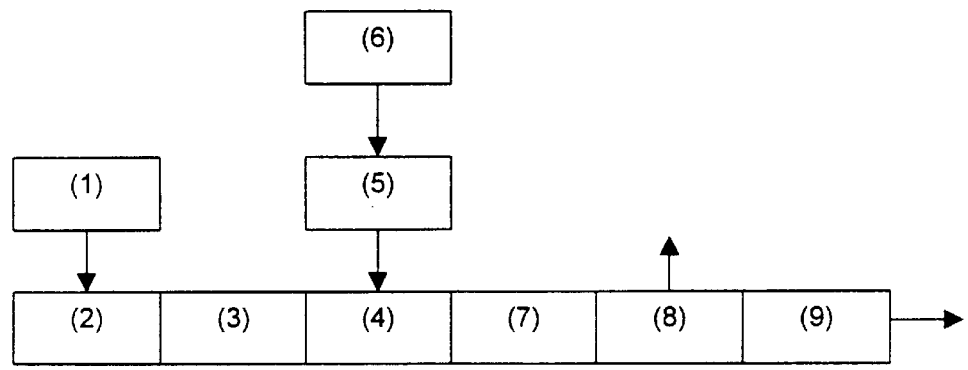
FIG. 1 shows a diagrammatic overview of the unit used to conduct the process of Example 1.

FIG. 1 shows a diagrammatic overview of the unit used to conduct the process.

The initial batch was supplied via a gravimetric metering system (1) to the filling section of a twin screw extruder.

The material was supplied via a first conveying process zone (2) to a second such zone (3) which mixed the material.

This was followed by a third process zone (4) which conveyed the material and to which component 2 was metered via a volumetrically operating toothed gear pump (5). The toothed gear pump was fed by a container thermally conditioned at 100° C. and subjected to pressure (p=6 bar) (6).

In the fourth process zone (7) the material was mixed.

In order to remove air and low-boiling constituents of the mixture, a devolatizing zone (8) is used.

Zone (9) is used for further homogenization and for building up pressure for forming the self-adhesive composition from a die.

To avoid damage to the active pharmaceutical substance, all process zones were thermally conditioned at 20° C.

The rotary speed of the extruder was 125 rpm. At the exit from the extruder, the composition had a temperature of between 75° C. and 85° C.

EXAMPLE 2

A prototype was produced using a twin screw extruder from the company Leistritz with a screw diameter of 50 mm, employing the following exemplary formulation B:

| No. | Component | | Weight fraction in % |
|---|---|---|---|
| 1 | Vistanex ® MM L-80 | high molecular mass polyisobutylene | 15 |
| 2 | Vistanex ® LM MH | low molecular mass polyisobutylene | 29 |
| 3 | AVICEL ® PH101 | Filler | 35 |
| 4 | Hyvis 2000 | Tackifier | 6 |
| 5 | Cetiol ® V | Plasticizer | 10 |
| 6 | Ibuprofen | active pharmaceutical substance | 5 |

Component 1 was granulated and provided with 5% by weight of component 3 as release agent.

Figure 2:
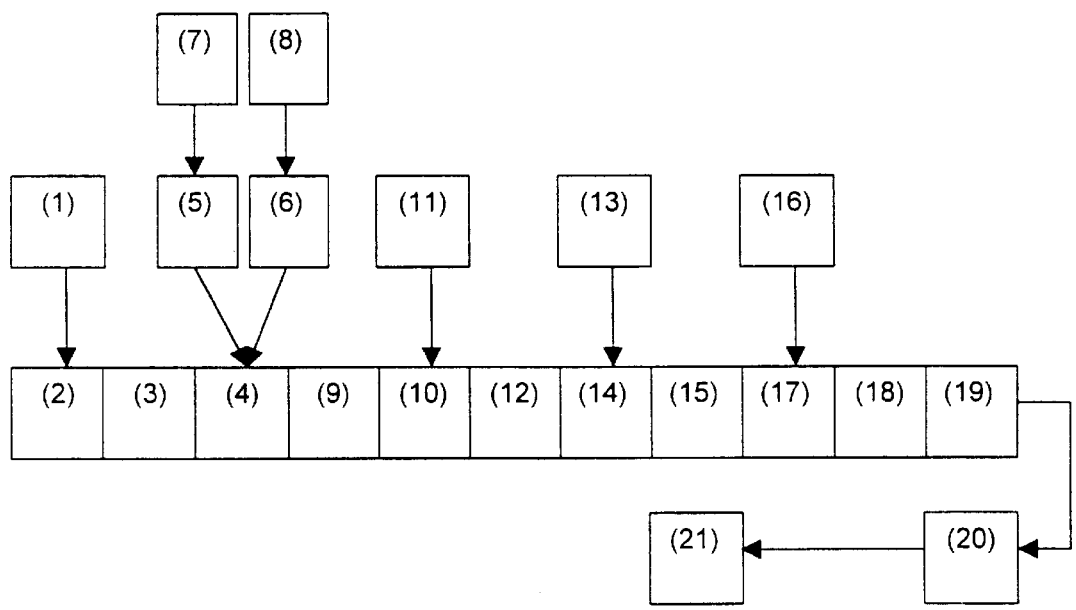
FIG. 2 shows a diagrammatic overview of the unit used to conduct the process of Example 2.

FIG. 2 shows a diagrammatic overview of the unit required to conduct the process.

The granules were supplied via a gravimetric metering system (1) to the filling section of the twin screw extruder.

The material was supplied via a first conveying process zone (2) to a second such zone (3) which mixed the material.

This was followed by a third process zone (4) which conveyed the material and to which components 2 and 4 were metered in via volumetrically operating toothed gear pumps (5)+(6). The toothed gear pumps were fed by containers (7, 8) thermally conditioned at 120° C. Subsequently, the material was mixed again (9).

In the next process zone (10) the material was conveyed, and component 3 was metered in gravimetrically (11).

After a further mixing zone (12), component 5 was added into a conveying zone (14) by way of a piston pump (13).

After a further mixing zone (15), component 6 was added to a conveying zone (17) by way of a gravimetric metering system (16). Subsequently, the material was mixed again (18).

The zone (19) was used for further homogenization and for pressure buildup. Subsequently, the self-adhesive composition was shaped via a 350 mm slot die (20) and discharged. The die gap was 300 µm. Subsequently, the composition was calendered in a calender unit (21) and laminated with two PET films.

To avoid damage to component 6, the temperatures of all process zones of the extruder were set at levels between 60° C. and 130° C.

The rotary speed of the extruder was 220 rpm. At the exit from the extruder, the composition had a temperature of 100° C. The slot die was thermally conditioned at 100° C.

What is claimed is:

1. A process for the continuous solvent-free and mastication-free production of self-adhesive compositions based on polyisobutylene with at least one active pharmaceutical substance in a continuously operating apparatus having a filling section and a compounding section, comprising the following steps:
   a) feeding an initial batch comprising granulated polyisobutylene, at least one release auxiliary and at least one active pharmaceutical substance into the filling section of the apparatus;
      optionally, feeding low molecular mass polyisobutylene, fillers, plasticizers, tackifiers, or resins or a combination thereof,
   b) transferring the feed components of the self-adhesive composition from the filling section to the compounding section,
   c) optionally, adding further components selected from the group consisting of low molecular mass polyisobutylene, fillers, plasticizers, tackifiers, resins and combinations thereof, to the compounding section,
   d) optionally, adding further pharmaceutical substances to the compounding section of the apparatus,
   e) preparing a homogeneous self-adhesive composition in the compounding section, and
   f) discharging the self-adhesive composition.

2. A process for the continuous solvent-free and mastication-free production of self-adhesive compositions based on polyisobutylene with at least one active pharmaceutical substance in a continuously operating apparatus having a tilling section and a compounding section, comprising the following steps:
   a) feeding an initial batch comprising granulated polyisobutylene, at least one release auxiliary into the filling section of the apparatus;
      and then feeding low molecular mass polyisobutylene, fillers, plasticizers, tackifiers or resins, or a combination thereof,
   b) transferring the feed components of the self-adhesive composition from the filling section to the compounding section,
   c) adding at least one pharmaceutical substance to the compound section and adding further components selected from the group consisting of low molecular mass polyisobutylene, fillers, plasticizers, tackifiers, resins, and combinations thereof to the compounding section,
   d) preparing a homogeneouS self-adhesive composition in the compounding section, and
   e) discharging the self-adhesive composition.

3. The process as claimed in either of claims 1 and 2, wherein the apparatus is a twin screw extruder having at least one metering port, and at least one devolatilization port.

4. The process as claimed in claim 1 or 2, wherein the temperature in the apparatus does not exceed 150° C.

5. The process as claimed in claim 1 or 2, wherein a melt pump or an extruder for conveying the self-adhesive composition is arranged between the apparatus and the coating device.

6. The process as claimed in claim 1 or 2, wherein self-adhesive composition is coated onto a web-form material, onto a release film or onto a release paper and optionally is lined with a further release film or a further release paper.

7. The process as claimed in claim 6, wherein coating of the web-form material takes place using an extrusion die.

8. The process as claimed in claim 6, wherein coating of the web-form material takes place using a roller or calender unit, the self-adhesive composition being shaped to the desired thickness as it passes through one or more roll nips.

9. The process as claimed in claim 6, wherein coating of the web-form material takes place using an extrusion die and a roll or calender unit, the self-adhesive composition being shaped to the desired thickness as it passes through one or more roll nips.

10. The process as claimed in claim 1 or 2, wherein at the exit from the apparatus the self-adhesive composition has a temperature of less than 150° C.

11. The process as claimed in claim 1 or 2, wherein the thickness of the self-adhesive composition on the web-form material is between 10 μm and 2000 μm.

12. The process as claimed in claim 1 or 2, wherein the active pharmaceutical substance fraction in the self-adhesive composition is between 0.001% by weight and 60% by weight.

13. The process of claim 3, wherein said twin screw extruders has between two and seven metering ports.

14. The process of claim 4, wherein said temperature does not exceed 140° C.

15. The process of claim 14, wherein said temperature does not exceed 130° C.

16. The process of claim 10, wherein said temperature of said self-adhesive composition at the exit from the apparatus is less than 130° C.

17. The process of claim 16, wherein said temperature of said self-adhesive composition at the exit from the apparatus is less than 110° C.

18. The process of claim 11, wherein said thickness is between 100 μm and 500 μm.

19. The process of claim 12, wherein said fraction is between 0.001% wt and 20% wt.

20. The process of claim 19, wherein said fraction is between 0.001% wt. and 10% wt.

* * * * *

UNITED STATES PATENT AND TRADEMARK OFFICE
CERTIFICATE OF CORRECTION

PATENT NO.   : 6,555,130 B2
DATED        : April 29, 2003
INVENTOR(S)  : Wustling et al.

It is certified that error appears in the above-identified patent and that said Letters Patent is hereby corrected as shown below:

Column 10,
Line 32, "having a tilling section" should read -- having a filling section --
Line 50, "homogeneouS" should read -- homogeneous --

Signed and Sealed this

Second Day of November, 2004

JON W. DUDAS
*Director of the United States Patent and Trademark Office*